United States Patent [19]

Dürsch et al.

[11] 4,220,610
[45] Sep. 2, 1980

[54] ORGANIC PHOSPHORUS COMPOUNDS WITH 2-HYDROXYALKYL-PHOSPHONIC ACID GROUPS

[75] Inventors: Walter Dürsch; Fritz Linke, 393.3, both of Königstein, Fed. Rep. of Germany

[73] Assignee: Hoechst Aktiengesellschaft, Fed. Rep. of Germany

[21] Appl. No.: 10,700

[22] Filed: Feb. 9, 1979

[30] Foreign Application Priority Data

Feb. 14, 1978 [DE] Fed. Rep. of Germany ....... 2806049

[51] Int. Cl.$^2$ .................. C07F 9/40; D06M 13/28
[52] U.S. Cl. .................. 260/928; 260/929; 260/953; 260/982; 427/393.3
[58] Field of Search ............... 260/928, 982, 953, 929

[56] References Cited

U.S. PATENT DOCUMENTS

| | | | |
|---|---|---|---|
| 3,298,967 | 1/1967 | Mason | 260/928 |
| 3,551,528 | 12/1970 | Randall | 260/982 |
| 3,855,360 | 12/1974 | Shim | 260/929 |
| 3,890,411 | 6/1975 | Shim | 260/928 |
| 4,096,208 | 6/1978 | Dursch et al. | 260/931 |

Primary Examiner—Anton H. Sutto
Attorney, Agent, or Firm—Connolly and Hutz

[57] ABSTRACT

Organic phosphorus compounds with 2-hydroxyalkyl-phosphonic acid groups of the general formula I

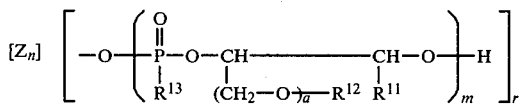

the individual symbols in the above formula I having the meaning as given in the description. The compounds, which are used as flame retardants for textile material, are prepared by reacting 1 mole of a compound of the general formula II $$Z_n(OH)_n \qquad (II)$$

with 1 to n.25 moles of 2-oxo-1,3,2-dioxa-phospholanes of the general formula III

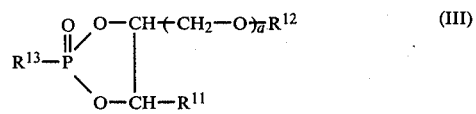

3 Claims, No Drawings

ORGANIC PHOSPHORUS COMPOUNDS WITH 2-HYDROXYALKYL-PHOSPHONIC ACID GROUPS

The demand for phosphorus compounds with crosslinkable hydroxyl groups has increased considerably in recent years. For example, in order to obtain optimum permanent flame-retardant finishes, in particular for textile floor coverings, water-soluble phosphorus compounds which are "tailor-made" depending on the chemical nature of the substrate and which have specific low or high hydroxyl numbers, a high phosphorus content and specific degrees of crosslinking are necessary.

Compounds containing phosphonic acid ester groups and hydroxyl groups in the molecule have already been obtained by oxalkylation of phosphonic acids with, preferably, ethylene oxide or propylene oxide. Particularly in the case of short-chain phosphonic acids, however, far more than the theoretically necessary 2 moles of alkylene oxide are required to achieve complete neutralization of the free acids. A proportion of the alkylene oxides is wasted in the form of (2-hydroxy-alkyl)-alkyl ether groups, which usually are undesired.

Furthermore, dialkyl phosphonates have already been converted by the action of di-halogeno-alkanes at temperatures of about 180° C. to oligomeric phosphonic acid esters, which in some cases have also subsequently been oxalkylated (U.S. Pat. No. 3,956,431). With this procedure methyl chloride or methyl bromide usually forms as an undesired by-product. Both of these compounds are readily volatile toxic compounds which, for reasons of environmental protection, have to be absorbed—relatively laboriously—and thus make production considerably more difficult.

The invention relates to organic phosphorus compounds with 2-hydroxyalkylphosphonic acid groups of the general formula I $$[Z_n] \left[ \begin{array}{c} [-OH]_{n-r} \\ \left( -O-\underset{\underset{R^{13}}{|}}{\overset{\overset{O}{\|}}{P}}-O-CH\underset{(CH_2-O)_aR^{12}}{|}-CH-O\underset{R^{11}}{|}H \right)_m \end{array} \right]_r \quad (I)$$

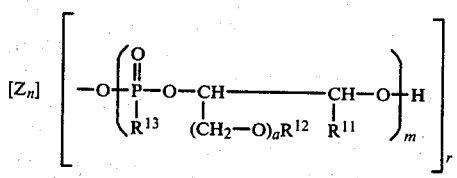

the individual symbols in the above formula I having the following meaning: n is an integer from 1 to 6 and preferably 1 to 4, r is an integer from 1 to n, that is to say from 1 to 6 and preferably the same number as n; m is 1 if r<n or is a number from 1 to 150 and preferably 2 to 10 if r=n; a is 0 or 1; $R^{11}$ is an optionally unsaturated and/or branched alkyl radical with 1-5 carbon atoms or, preferably, hydrogen, $R^{12}$ is an optionally unsaturated and/or branched alkyl radical with 1-22 and preferably 1-3 carbon atoms, which optionally can be substituted by 1 or two chlorine or bromine atoms, or a cycloalkyl radical with 6-10 carbon atoms, an aryl or aralkyl radical with up to 18 C atoms, such as, in particular, phenyl or benzyl, or crotonyl, acroyl or methacryl or—but only if a =0—particularly preferentially also hydrogen, and $R^{13}$ has the same meaning as $R^{12}$ with the exception of hydrogen and is preferably ($C_1$-$C_3$)-alkyl and can additionally be a monovalent phosphorus-containing radical of the formula $R_p^{13}$ $$R^{15}\!-\!(O)_b\!-\!\underset{\underset{(O)_cR^{16}}{|}}{\overset{\overset{O}{\|}}{P}}\!-\!R^{14}\!-\!\quad (R_p^{13})$$

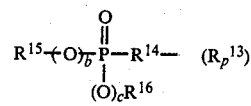

in which b and c represent 0 or 1, $R^{14}$ represents $C_1$-$C_{10}$-alkylene, cycloalkylene, arylene or aralkylene and preferably represents ($C_1$-$C_6$)-alkylene, and also $R^{15}$ and $R^{16}$ represent optionally unsaturated and/or branched $C_1$-$C_5$-alkyl radicals and preferably represent methyl or ethyl; and $z_n$ is a n-valent radical from the group comprising straight-chain or branched aliphatic or araliphatic hydrocarbon radicals with 1 to 22 and preferably 1-8 C atoms, which optionally can be interrupted by up to two carboxylato groups (—O—CO—) or up to 2 —S— and/or $NR^2$ radicals in which $R^2$=($C_1$-$C_4$)-alkyl, especially methyl, and/or substituted by fluorine, chlorine or bromine atoms or optionally unsaturated carboxylato groups or carboxamide, carbamate or urea groups or by primary, secondary or tertiary amino groups, or hydrocarbon radicals which contain ether groups and have equivalent weights of up to 8000 and preferably up to 4000 and are obtained by oxethylation and/or oxpropylation of n-valent aliphatic, araliphatic or aromatic hydroxy compounds, amines and/or mono- or di-carboxylic acids with 1-22 and preferably 1-10 C atoms, in which the araliphatic or the aromatic radicals are derived from benzene, alkyl- or alkylene-benzenes with up to 18 C atoms, naphthalene, diphenyl, diphenylmethane, diphenylethane or 2,2-diphenylpropane and optionally can be substituted in the nucleus by 1 or 2 methoxy or ethoxy groups or can be substituted, preferably up to pentasubstituted, in the nucleus and/or on the side chains by F, Cl or Br atoms, or phosphorus-containing radicals of the general formula $$R^2-(O)_{d_1}-\underset{\underset{O}{\|}}{\overset{\overset{R^1}{|}}{P}}-(O)_{d_2}-R^3 \quad Z_{n,1}$$

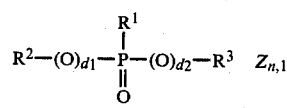

in which $d_1$ and $d_2$ independently of one another are 0 and 1 and $R^1$ is alkyl, hydroxyalkyl, optionally ($C_1$-$C_2$)-alkylated or -dialkylated aminoalkyl, halogeno- (preferably Cl-)alkyl with 1 to 3 C atoms, alkenyl with 2 or 3 C atoms or phenyl, which optionally can be substituted by 1 or 2 halogen atoms, preferably Cl or Br, and $R^2$ and $R^3$ have the same meaning as $R^1$ with the proviso that at least one of the radicals $R^2$ or $R^3$ is an alkylene radical with 2-5 C atoms, or phosphorus-containing radicals of the general formula $$\begin{array}{c} R^3-O \\ R^2-(O)_{d_1} \end{array}\!\!\!\underset{\underset{O}{\|}}{P}\!-\!R^4\!-\!\underset{\underset{O}{\|}}{P}\!\!\!\begin{array}{c} O-R^3 \\ (O)_{d_1}R^2 \end{array} \quad Z_{n,2}$$

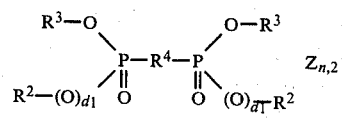

in which $d_1$, $R^2$ and $R^3$ are as defined in $Z_{n,1}$ and $R^4$ denotes a straight-chain or branched ($C_1$-$C_6$)-alkylene, phenylene or xylylene radical or a radical in which

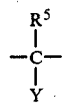

Y=OH or NH$_2$ and R$^5$ is (C$_1$–C$_3$)-alkyl, or phosphorus-containing radicals of the general formula

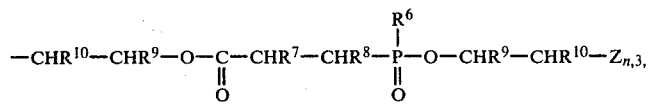

in which R$^6$ denotes a (C$_1$–C$_4$)-alkyl group, which optionally can be substituted, preferably monosubstituted, by halogen, especially chlorine, or a cycloalkyl group with up to 8 C atoms, especially cyclophetyl or cyclohexyl, an alkylene group with up to 4 C atoms, especially vinyl and allyl, or a phenyl or benzyl group which optionally can be substituted, preferably monosubstituted to trisubstituted, by halogen, preferably chlorine and/or bromine, R$^7$ denotes hydrogen or a (C$_1$–C$_4$)-alkyl group, preferably methyl, and R$^8$ is hydrogen or a (C$_1$–C$_2$)-alkyl group, preferably methyl, at least one of the radicals R$^7$ and R$^8$ being hydrogen, R$^9$ denotes hydrogen, methyl or chloromethyl and R$^{10}$ denotes hydrogen, methyl or ethyl, preferably hydrogen, The compounds of the formula I are obtained by a so-called phosphono-1,2-alkoxylation, by reacting 1 mole of a compound of the general formula II $$Z_n(OH)_n \qquad (II)$$

with 1 to n.20 moles of 2-oxo-1,3,2-dioxa-phospholanes of the general formula III

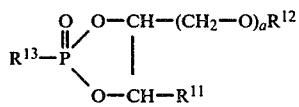

in which formulae n, a, Z, R$^{11}$, R$^{12}$ and R$^{13}$ are as defined above.

The alcohols of the formula II $Z_n$(—OH)$_n$ are all accessible by known methods. Amongst the monohydric organic hydroxy compounds with n=1 which can be employed, suitable compounds are, for example, all readily accessible aliphatic straight-chain and branched alcohols with 1 to 22 C atoms. The following may be mentioned, for example, as the most important: methanol, ethanol, n-propanol, i-propanol, n-butanol, sec.-butanol, n-hexanol, 2-ethyl-butan-1-ol, n-octanol, 2-ethyl-hexan-1-ol, n-dodecanol, n-hexadecanol and n-octadecanol, the alcohols with 1 to 4 C atoms being preferred. Polyhydric alcohols with n=2–6 are even more suitable than monofunctional alcohols.

Examples of polyhydric aliphatic polyols with n=2–6 which may be mentioned are: ethylene glycol, 1,2-propylene glycol, 1,3-propylene glycol, 1,4-butanediol, neopentylglycol, 1,6-hexanediol, glycerol, trishydroxymethylethane, trishydroxymethylpropane, pentaerythritol, sorbitol and mannitol. Glycerol and pentaerythritol are particularly suitable.

Examples of unsaturated alcohols which may be mentioned are: n-but-2-en-1-ol, 1,4-butenediol and allyl alcohol, 1,4-butenediol being the preferred dihydric alcohol.

Amongst the numerous compounds in which one or more —CH$_2$ groups in an aliphatic hydrocarbon radical have been replaced by ether bridges —O—, suitable compounds are, for example, the reaction products of monohydric alcohols with one or more molecules of alkylene oxides or alkylene carbonates, such as, for example, 2-methoxyethanol, 2-ethoxyethanol, 2-n-butoxy-ethanol, 2-(2'-ethyl-hexyloxy)-ethanol and 2-n-dodecyloxy-ethanol, and also the reaction products of 1 mole of methanol, 1 mole of ethanol or 1 mole of isopropanol and 2 moles of ethylene oxide or an alkylene carbonate, that is to say so-called methyldiglycol, ethyldiglycol and isopropyldiglycol, and also reaction products of 3 to 100 molecules of ethylene oxide or ethylene carbonate with 1 mole of methanol, ethanol, isobutanol, dodecanol, oleyl alcohol and the like.

Suitable reaction products of ethylene oxide and dihydric alcohols are, for example, so-caled diglycol, so-called triglycol and the higher reaction products of ethylene oxide and/or ethylene carbonate with water or ethylene glycol, the so-called polyethylene glycols of various molecule sizes up to an average molecular weight of 8,000, especially diglycol and triglycol, and further suitable compounds are, for example, the adducts of 1–150 molecules of ethylene oxide and/or ethylene carbonate with trihydric or higher hydric alcohols (n=3–6), such as, for example, glycerol, trishydroxymethylpropane, pentaerythritol and the like.

In addition to reaction products of ethylene oxide and/or ethylene carbonate with monohydric or polyhydric alcohols, reaction products of monohydric and polyhydric alcohols with other 1,2-alkylene oxides and/or 1,2-alkylene carbonates, such as, in particular, 1,2-propylene oxide, 1,2-propylene carbonate or epichlorohydrin, can also be used, as can the reaction products of ethylene oxide and/or ethylene carbonate with poly-1,2-propylene glycols, which, as is known, are manufactured in a wide variety as surface-active compounds. Compounds which may be mentioned in particular are corresponding poly-1,2-propylene glycols and corresponding adducts of ethylene oxide and/or ethylene carbonate with (poly)-1,2-propylene oxides with molecular weights of up to 8,000 and preferably of up to 4,000.

In addition to —O— bridges, the hydrocarbon chain of aliphatic hydroxy compounds can also be interrupted or substituted by other hetero-atoms, such as, for example, by the elements N, S and/or P or carboxylic acid ester groups. These compounds can be obtained, for example, particularly simply by reacting one or more molecules of 1,2-alkylene oxides and/or 1,2-alkylene carbonates with ammonia, primary or secondary amines, hydrogen sulfide or mercaptans and with oxyacids of phosphorus or (C$_2$–C$_6$)-carboxylic acids or -dicarboxylic acids.

Examples which may be mentioned of the reaction products of these compounds with 1,2-alkylene oxides or 1,2-alkylene carbonates are:

With N in the molecule: monoethanolamine, diethanolamine, 1-amino-n-butan-4-ol, tertiary alkanolamines, such as, for example, triethanolamine, methyldiethanolamine, n-butyl-diethanolamine, tetra-hydroxyethyl-ethylenediamine, pentahydroxyethyl-diethylenetriamine, n-dodecyl-diethanolamine, dimethylethanolamine, n-butyl-methyl-ethanolamine, di-n-butyl-ethanolamine and n-dodecylmethyl-ethanolamine and correspondingly higher reaction products of these tertiary amines with up to 150 moles of ethylene oxide or ethylene carbonate or propylene oxide or propylene carbonate.

With S in the molecule: bis-(2-hydroxyethyl)-sulfide, bis-(2-hydroxypropyl) sulfide, bis-(2-hydroxyethyl)-sulfone and their reaction products with further ethylene oxide or ethylene carbonate or propylene oxide or propylene carbonate up to molecular weights of 8,000.

With P in the molecule: neutral reaction products of 1,2-alkylene oxides such as ethylene oxide, propylene oxide or epichlorohydrin, above all ethylene oxide or, for example, ethylene carbonate, with monobasic and polybasic alkanephosphonic acids with 1 to 18 C atoms, such as, for example, with n-butane-, isobutane-, 2-ethyl-hexane-, n-octane-, decane-, dodecane-, or tetradecane-phosphonic acid, but especially with methane-, ethane-, propane- and vinyl-phosphonic acid and 1,2-ethanediphosphonic acid, and also with monobasic or polybasic dialkyl-phosphinic acids, such as, for example, methyl-butyl-phosphinic acid, methyl-n-octyl-phosphinic acid, methyl-n-dodecyl-phosphinic acid and especially dimethyl-, ethyl-methyl-, methyl-propyl- or methyl-vinyl-phosphinic acid and ethane-1,2-bis-(methyl-phosphinic acid); and, furthermore, also reaction products of 1 to 7 moles of alkylene oxide or ethylene carbonate with monobasic aliphatic carboxylic acids, such as, for example, crotonic acid and above all acetic acid, propionic acid or butyric acid, and polybasic aliphatic carboxylic acids, such as, for example, succinic acid and adipic acid.

In addition to hydroxy compounds of this type which contain hetero-atoms N, S and P and are very easily accessible by oxalkylation reactions, numerous further compounds which contain hydroxyl groups and optionally these hetero-atoms and/or carboxylic acid ester groups in the hydrocarbon chain are also suitable and amongst these mention is made only of, for example, oligo-condensation products, which are formed by reacting dicarboxylic acids with polyhydric alcohols, and also methyl glycollate, ethyl 2-hydroxyethane-carboxylate and the like.

Further suitable compounds are, for example, dimethyl hydroxymethane-phosphonate, diethyl 2-hydroxyethane-phosphonate, di-n-butyl 3-hydroxypropane-phosphonate and the like, and analogous compounds of the phosphinic acid series, such as, for example, methyl hydroxymethyl-methyl-phosphinate, ethyl 2-hydroxyethyl-methyl-phosphinate, 2'-ethyl-hexyl 3-hydroxypropyl-methyl-phosphinate, hydroxymethyl-dimethylphosphine oxide and 2-hydroxyethyl-dimethyl-phosphine oxide.

All of the said aliphatic hydroxy compounds, and analogous aliphatic hydroxy compounds which have not been named, can be substituted by the halogen atoms chlorine, bromine and fluorine, especially by chlorine and bromine. Compounds which may be mentioned are, for example, the following compounds, which are readily accessible and of interest because of their advantageous flameproofing characteristics: 2-bromoethanol, 2,3-dibromopropan-1-ol, 2,3-dibromo-butane-1,4-diol, bis-(2-hydroxyethyl) dibromosuccinate, bis-(2-hydroxyethyl)-2,3-dibromopropane-phosphonate, bis-(2,3-dibromopropyl) 2-hydroxyethane-phosphonate and also chloroethanol, 2,3-dichloro-propan-1-ol, 1,3-dichloro-propan-2-ol, 2,3-dichloro-butane-1,4-diol, bis-(2,3-dichloro-propyl) 2-hydroxyethane-phosphonate, bis-(2-hydroxyethyl) 1-chloro-vinyl-phosphonate and the like.

The choice of suitable ether group-containing aromatic compounds which carry n-OH radicals is also very wide. Compounds which can be used are all oxalkylation products of so-called phenols in the broader sense, such as, for example, phenol, pyrocatechol, resorcinol, hydroquinone, pyrogallol, hydroxyhydroquinone, phloroglucinol, the various tetra- and penta-hydroxybenzenes, hexahydroxybenzene, α-naphthol and β-naphthol, and also of hydroxynaphthalenes containing more than one hydroxyl group, such as, for example, 1,2-, 1,3-, 1,4-, 1,5-, 1,6-, 1,7-, 1,8- and 2,3-dihydroxy-naphthalene, and also 4-hydroxydiphenyl, 4,4'-dihydroxy-diphenyl and - because of the advantageous price—above all of 2,2-bis-(4-hydroxyphenyl)-propane-and 4,4'-bis-(4-hydroxy-phenyl)-methane with molecular weights of up to 8,000. The oxalkylates of partially etherified polyhydric aromatic hydroxy compounds, such as, for example, hydroquinone monomethyl ether, resorcinol monoethyl ether and the like, are also suitable.

Because of the advantageous influence on the flame-proofing characteristics, aromatic chlorohydroxy and especially bromohydroxy compounds are of particular interest, such as, for example, the 2-hydroxy-ethyl ethers of 2,4,6-tribromo-phenol, pentabromo-phenol, 2,4,6-trichloro-phenol or pentachlorophenol and 2,2-bis-(4-hydroxy-3,5-dibromophenyl)-propane.

Further suitable compounds are the oxalkylates of aromatic hydroxy compounds with alkyl side groups with a total of up to 18 C atoms, such as, for example, of o-, m- or p-cresol, thymol, 4-tert.-butyl-phenol, n-nonyl-phenol and isotridecylphenol with molecular weights of up to 8,000.

Amongst the araliphatic and aromatic compounds, further suitable compounds are all araliphatic compounds containing alcoholic hydroxyl groups, such as, for example, benzyl alcohol and all 2-hydroxyalkyl esters which are formed by oxalkylations of aromatic compounds which contain free carboxylic acid radicals, phosphonic acid radicals or phosphinic acid radicals.

Therefore, compounds which can be used for the reaction with 1,2-alkylene oxides or 1,2-alkylene carbonates in order to manufacture aromatic starting materials II with alcoholic hydroxyl groups are, in addition to the aromatic compounds with phenolic hydroxyl groups which have already been mentioned, above all, for example, aromatic mono- and di-carboxylic acids, such as, for example, benzoic acid, phthalic acid, isophthalic acid, terephthalic acid, 1-naphthalenecarboxylic acid, 2-naphthalenecarboxylic acid and the diverse naphthalenedicarboxylic acids, but also aromatic hydroxycarboxylic acids, such as, for example, the three different hydroxy-benzoic acids, the various naphthol-carboxylic acids, 4,4'-diphenyl-dicarboxylic acid and the like.

Likewise, for example, all other aromatic carboxylic acids which contain bromine, chlorine or fluorine and are derived from benzene and naphthalene, such as, above all, for example, tetrabromo- and tetrachlorophthalic acid, are suitable.

Likewise, aromatic phosphonic and phosphinic acids, such as, for example, benzenephosphonic acid, 1,3- and 1,4-phenylene-diphosphonic acid, phenyl-methyl-phosphinic acid, 1,3- and 1,4-phenylene-bis-(methyl-phosphinic acid) and the like, can be converted to the corresponding 2-hydroxyalkyl esters by reaction with the 1,2-alkylene oxides and/or 1,2-alkylene carbonates.

Suitable aromatic compounds with alcoholic hydroxyl groups can, however, also be obtained by prior reactions of aromatic amines or mercapto compounds with 1,2-alkylene oxides and/or 1,2-alkylene carbonates.

Examples which may be mentioned of compounds which contain aromatic amino groups and are suitable for oxalkylations are: aniline, methylaniline, o-, m- and p-phenylenediamine, the diverse o-, m- and p-toluidines and -anisidines, -aminophenols and -amino-benzoic acids, naphthylamines, the diverse amino-naphthols and also 4,4'-diaminodiphenylmethane, 4,4'-benzidine, the possible chloro- and bromoanilines and, above all, 2,4,6-tribromoaniline and the like, but also phenylalkylamines, such as, above all, benzylamine or methylbenzylamine and dibenzylamine.

Examples which may be mentioned of aromatic mercapto compounds which can be oxalkylated are: phenylmercaptan, p-toluyl-mercaptan, 1- and 2-naphthylmercaptan and the like.

Amongst all of the compounds II with alcoholic hydroxyl groups, particularly preferred compounds are those which additionally contain crosslinkable methylolizable or polymerizable radicals, such as, for example, 2-hydroxyethyl carbamate, 2-hydroxyethylurea, 2-hydroxyethyl-methacrylic acid esters and the like.

In each case only one compound can be employed under the formula II, but it is also possible to use mixtures of several compounds II. Mixtures of compounds I are then correspondingly obtained.

The 2-oxo-1,3,2-dioxa-phospholanes of the general formula III can be obtained, for example, from the corresponding phosphonic acid dichlorides of the general formula IV

(IV)

and diols of the general formula V

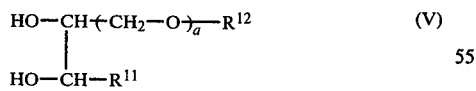
(V)

in the presence of HCl acceptors, such as, above all, for example, of tertiary amines. (Compare, for example, German Offenlegungsschrift 2,455,700).

However, it is also possible to synthesize compounds III in which a is 0 by an addition reaction of 1,2-alkylene oxides with phosphonic acid anhydrides. (Compare J. of General Chemistry of the USSR, Vol. 35, No. 4, pages 731–735 (1965)). The compounds of the formula III in which a is 1, which have not been previously described in the said publication and which are derived not from 1,2-alkylene oxides but, for example, from glycidyl ethers of aliphatic alcohols and of phenols can be manufactured analogously.

Compounds containing $R_P^{13}$ radicals of the formula III$_p$

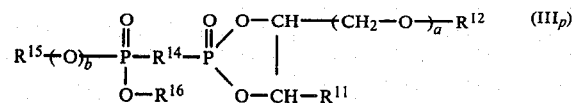
(III$_p$)

can be obtained, for example, by an Arbuzov reaction of compounds III in which $R^{13}$ represents bromo- or chloro-alkyl radicals with trialkyl phosphites (b=1) or dialkylphosphonic acid esters (b=0).

The large number of suitable compounds III results from combination of the various variable radicals $R^{13}$, $R^{12}$, $R^{11}$ and a.

Amongst the many compounds of the formula III, individual compounds which are suitable are, for example:

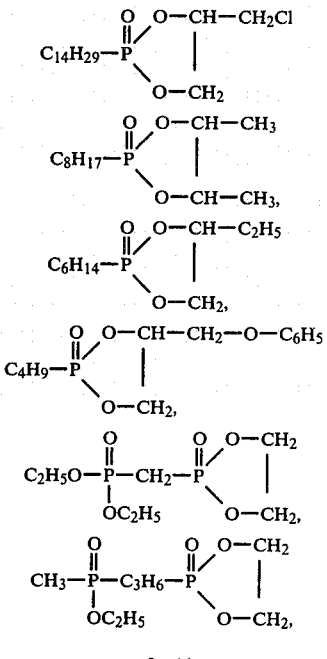

preferably

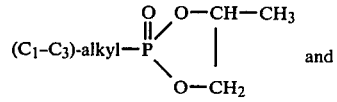
and particularly preferentially

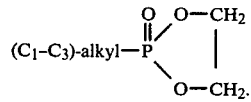

In each case only one compound can be employed under the formula III, but it is also possible to use mixtures of several compounds of the formula III. Mixtures of compounds of the formula I are then obtained.

The molar ratios between the 2-oxo-1,3,2-dioxaphospholanes (III) and the alcohols II can vary within wide limits, depending on the desired phosphorus content and hydroxyl group content. They can be between (1/n) and n.m. This means that 1 mole of an alcohol $Z_n(-OH)_n$ can be reacted with 1 to m.n (or 150.n) moles of III. The greater the number of moles of III reacted per mole of II, the higher becomes the P content of the reaction products and the lower becomes the hydroxyl group contents or the "hydroxyl numbers" (OHN). A maximum of up to m=150 moles and preferably m=2–8 moles of III can be added on per hydroxyl group.

The reactions of the compounds II and III must be carried out in the absence of water. In many cases, and above all if the compounds II and III are liquids of low viscosity, the use of solvents is superfluous. However, if the compounds II and/or III are substances which are solid at the reaction temperatures chosen, it is advisable to add anhydrous, inert, relatively polar solvents or diluents, which should be as readily volatile as possible, such as, above all, for example, tetrahydrofuran, dioxane, acetone, 1,2-dimethoxy-ethane, acetonitrile and the like. After the reactions have been carried out, these solvents or diluents must be removed again under conditions which are as mild as possible—optionally in vacuo.

The reaction can also be carried out in the absence of catalysts. However, alkaline catalysts accelerate the reaction greatly. Strongly alkaline catalysts which can be used are, in particular, the alkali metals lithium, potassium and, preferably, sodium, sodium amide, sodium hydride and preferably alkali metal alcoholates, such as, above all, sodium ethylate and, because of the low degree of discoloration, sodium methylate in the form of high percentage strength solutions in methanol. By mixing sodium methylate solution with the compounds I and stripping off the methanol in vacuo at temperatures which are as low as possible it is possible, for example, very easily to produce alcoholates of the alcohol II which is used and these alcoholates are outstandingly suitable as alkaline catalysts. Weakly alkaline catalysts, such as, for example, sodium carbonate or potassium carbonate, accelerate the reaction only at elevated temperatures of about 60°–200° C.

The molar amounts of alkaline catalysts depend especially on the number of moles of compounds III.

It is advisable to use 0.002–0.5 mole and preferably 0.01 to 0.1 mole of alkaline catalysts per mole of the compound III.

A portion of the alkaline catalyst is consumed by side reactions, above all by saponification of phosphonic acid ester groups. In order to discern whether adequate amounts of free alkali are present it is advisable to add indicators, preferably indicators which are colorless in the neutral pH range, such as, for example, phenolphthalein or preferably thymolphthalein.

If necessary, excess free alkali can be neutralized after the end of the reaction by adding calculated amounts of inorganic or organic acids or acid donors, such as, for example, sulfuric acid, phosphoric acid, ethanephosphonic acid, acetic acid, oxalic acid, acetic anhydride and the like.

The reaction temperatures can vary between about −20° C. and 200° C. They are highly dependent on whether alkaline catalysts are used at all and on whether the reaction medium is alkaline or not. Preferred temperature ranges are 100°–170° C. in the absence of catalysts and 0°–40° C. in the presence of strongly alkaline catalysts, that is to say in an alkaline medium. The reaction times are from 1 minute to about 48 hours and preferably 5 minutes to 20 hours. At higher temperatures and especially in the absence of alkaline catalysts or in the neutral pH range and in the weakly acid pH range, considerably longer reaction times of preferably about 1–20 hours are necessary. In the presence of strong alkaline catalysts, preferably 5 minutes to 2 hours suffice. The reaction, especially when small molecules of II and III are employed, is in some cases highly exothermic, so that, if necessary, the reaction mixture must be cooled intensively while III is added to II and it is particularly advisable to add the compounds III in portions to the mixtures of the alcohols II and the corresponding alcoholates. It is true that it is also possible to mix the compounds II and III and to add solutions of alkaline catalysts (for example solutions of sodium methylate in methanol) dropwise. However, there is then always a danger that the reaction mixture will overheat and/or that (usually undesired) saponification of considerable numbers of phosphonic acid ester groups will take place. The above applies similarly for the case where only the 2-oxo-1,3,2-dioxa-phospholanes III are initially introduced and the alcohols II are introduced slowly as a mixture with or at the same time as the alkaline catalysts. At low reaction temperatures, the reaction is always interrupted if the pH value falls below about 5–7 (measured with moist indicator paper).

The resulting reaction products of the formula II are in most cases colorless oils but sometimes, for example when longer-chain saturated fatty alcohols are used, also pasty or waxy. Their hydroxyl numbers (=mg of KOH per gram) can vary within wide limits between about 10 and about 900 and preferably between 40 and 300.

It is noteworthy that, with the preferred manufacturing process; that is to say in the alkaline pH range, the addition reaction of the compounds III and the alcohols II already takes place very readily and rapidly at relatively very low reaction temperatures and that, moreover, primary and secondary amino groups do not react. As a result of this, it is also possible to use alcohols II which contain any desired amino groups or radicals which cannot be subjected to heat, such as, for example, methacryl, carbamate and urea radicals and the like.

The compounds of the formula I are valuable intermediate products for numerous phosphorus-organic compounds. The fact that even those alcohols of the formula II which are not naturally water-soluble, for example because they contain a longer-chain alkyl group, can be converted to water-soluble adducts by reaction with low-molecular compounds of the formula III is also of particular interest in this context. These compounds I, above all if they are derived from low-molecular polyhydric or monohydric crosslinkable aliphatic alcohols, can, however, also be used direct as flame retardants for textile material. For this purpose, they are fixed on the textile material by known processes, using reactive crosslinking agents, if necessary in the presence of crosslinking catalysts. An excellent flame-retardant effect is obtained in this way.

Those compounds according to the invention which contain terminal hydroxyl groups are permanently crosslinked with polyfunctional N-methylol compounds of melamine, urea or cyclic urea compounds in the presence of acid catalysts. On the other hand, if these compounds contain terminal vinyl groups they can be polymerized or co-polymerized with or without other vinyl group-containing compounds in the presence of a polymerization catalyst. The high polymer compounds obtained in this way are also distinguished by good permanence on diverse textile materials.

Crosslinking polyfunctional N-methylol compounds which can be used are, for example, derivatives of amino-1,3,5-triazines, such as trimethylolmelamine, hexamethylolmelamine, trimethylolmelamine trimethyl ether, hexamethylolmelamine pentamethyl ether, trimethylolmelamine triisobutyl ether and dimethylol-acetoguanamine, and also derivatives of urea, such as dimethylolurea, dimethylolurea dimethyl ether, dimethylolurea dibutyl ether, dimethylolcycloethyleneurea, dimethylolcyclopropyleneurea, dimethylol-4-methoxy-5-dimethylpropyleneurea and dimethylol-5-hydroxypropyleneurea, 1,3-dimethylol-4,5-dihydroxy-imidazolid-2-one, 1,3-dimethylol-5-hydroxyethylhexahydrotriazin-2-one, dimethylolurone and dimethylolcarbamates, such as, for example, methyl dimethylolcarbamate, hydroxyethyl dimethylolcarbamate and methoxyethyl dimethylolcarbamate.

Interesting compounds, which have proved particularly suitable, are the melamine derivatives, for example trimethylolmelamine trimethyl ether or hexamethylolmelamine pentamethyl ether.

The catalysts, which show their action in the acid pH range, which are added are in general about 0.2 to 5% by weight and preferably 0.4 to 3% by weight of inorganic or organic acids or their salts which liberate acid on hydrolysis or on heat treatment, such as, for example, sulfuric acid, hydrochloric acid, phosphoric acid, trichloroacetic acid, maleic acid, tartaric acid, citric acid or acetic acid or their salts with ammonia, amines or polyvalent metals, preferably salts of strong or medium strength acids, such as ammonium sulfate, ammonium chloride, mono- and di- ammonium oxalate, ammonium nitrate, magnesium chloride, aluminum chloride, zinc chloride, zinc nitrate, zinc fluoborate and 2-amino-2-methyl-propanol hydrochloride.

The crosslinking catalysts can be added to the finishing liquors on their own or as mixtures with one another. Such finishing liquors, which are preferably aqueous, contain in general 2 to 5% by weight and preferably 2.5–4.5% by weight of compounds of the formula I and also 5 to 10% by weight and preferably 7 to 9% by weight of crosslinking substances, as indicated above, and also 0.2 to 5% by weight of crosslinking catalysts, and also, optionally, 5 to 25% by weight of high polymers, preferably in the form of dispersions.

The good polymerizability of the phosphorus compounds according to the invention which contain vinyl groups enables them to be polymerized on textile substrates under conditions customary in textile technology, even when the substrate area is large, even without a blanketing inert gas and in the presence of atmospheric oxygen. The polymers thus obtained impart a good flameproofing effect to very diverse textile sheet-like structures.

In general, free radical donors are added to the finishing liquors as polymerization catalysts, but it is also possible to produce free radicals on the fiber material, for example during the treatment with energy-rich radiation.

The polymerization catalysts used are the compounds known for the polymerization of acrylates, that is to say, for aqueous finishing liquors, for example potassium peroxydisulfate (persulfate) or ammonium peroxydisulfate (persulfate), hydrogen peroxide or hydrogen peroxide donors such as $NH_4P_2O_7.H_2O_2.H_2O$ or $(NH_2CONH_2).H_2O_2$ (termed carbamide-hydrogen peroxide in the examples), and also redox catalyst systems, such as hydrogen peroxide and ascorbic acid or sodium bisulfite, manganese-II chloride or iron-II chloride and sodium bisulfite, sodium chlorate/sodium bisulfite or sodium carbonate/sodium bisulfite.

In order to increase the permanence, and especially the stability of the flameproofing effect obtained according to the invention to washing, it is particularly advantageous to add to the monomers of the formula I further comonomers, especially those which have a crosslinking action. Examples of such comonomers are, above all, acrylamide, N-methylol-acrylamide, methylene bis-acrylamide, N-methylolmethylene-bis-acrylamide, N,N'-dimethylol-methylene-bis-acrylamide, N-formamidomethyl-acrylamide, divinylbenzenes, triallylcyanuric acid esters, imides and anhydrides of acrylic acid and methacrylic acid and 1,3,5-trisacryloylhexahydro-1,3,5-triazine.

If comonomers which contain —C≡C— groups and also contain further reactive groups are used, for example acrylamide or N-methylol-containing compounds, such as, for example, N-methylol-methylene-bis-acrylamide or N,N'-dimethylolmethylene-bis-acrylamide, yet further or additional crosslinking components can be added to the system, such as, for example, derivatives of amino-1,3,5-triazines such as trimethylolmelamine, hexamethylolmelamine or hexamethylolmelamine pentamethyl ether, and also derivatives of urea, such as dimethylolurea, dimethylolurea dimethyl ether, didimethylolcycloethyleneurea or dimethylolcyclopropyleneurea, or dimethylolcarbamates, for example methyl dimethylolcarbamate, ethyl dimethylolcarbamate and the like.

In total, these additives to the monomers of the formula I amount to 10–300 parts by weight, preferably 30 to 180 parts by weight and especially 40–120 parts by weight per 1,000 parts by weight of substrate.

The textile fiber materials on which the flame-retardant finishes can be carried out by the possible crosslinking methods described above, both by the condensation process and also by the polymerization process, vary. Materials which can be used are woven fabrics, knitted fabrics, nonwoven fabrics, for example needle-punched nonwovens for wall and floor coverings and tufted or woven carpets. Woven fabrics and knitted fabrics can consist of natural or regenerated cellulose fibers or of synthetic fibers or of mixtures thereof and nonwoven fabrics can consist of cellulose fibers or synthetic fibers, for example needle-punched nonwoven broadloom carpeting which consists of 100% polyamide 6 fibers or of 50/50 polyester/polyamide fibers or such carpeting which has a polyester core (underside) and a walking surface of polyamide 6 fibers, 50/50 polyamide fibers and viscose staple, 50/50 polyesters fibers and viscose staple and 100% polyester fibers.

Good permanent flameproofing effects are also obtained on fiber material which consists of 100% polypropylene fibers or of polypropylene fiber mixtures, for example with polyester or polyamide or cellulose fibers.

Surprisingly, very good flame-retardant effects are also obtained when the flame-retardant phosphorus-organic compounds are incorporated with the above-mentioned crosslinking products and catalysts in a precoat impregnating liquor for tufted carpets or in a back finishing liquor for woven carpets.

The base fabric of the tufted carpets can consist of cotton, jute, viscose staple, wool or synthetic fibers based on polyamide, polyesters or polypropylene or a mixture, or of glass fibers. Needle-punched nonwovens of polyester or polypropylene fibers are also outstandingly suitable as the base fabric. The tufted pile (loop or cut pile) can consist of polyamide, polyester or polyacrylonitrile fibers. Mixtures of polyacrylonitrile fibers with, for example, 20% polyester fibers have also proved suitable.

In order to modify the handle, to obtain good dimensional stability and to improve the wear and the firmness underfoot of needle-punched nonwoven broadloom carpeting, dispersions of high polymer plastics are added to the finishing liquors.

The binding of the pile filaments in tufted goods into the base fabric described above is effected by the so-called pre-coat with dispersions of high polymer plastics, to which the flame-retardant components according to the invention, crosslinking agents and catalysts are added.

Plastic dispersions which can be used are polyvinyl acetate, polyvinyl acetate with plasticizers for plastics, such as dibutyl phthalate, copolymers of vinyl acetate with dibutyl maleate, copolymers of butyl acrylate with N-methylolacrylamide, copolymers of butyl acrylate, N-methylolacrylamide and acrylic acid, copolymers of butyl acrylate, N-methylolacrylamide and/or N-methylolmethacrylamide and acrylic acid, copolymers of butyl acrylate, methyl methacrylate and methylolmethacrylamide, copolymers of butyl acrylate, acrylonitrile, N-methylolacrylamide and methacrylic acid, copolymers of butyl acrylate, acrylonitrile, N-methylolmethacrylamide and acrylic acid, copolymers of butyl acrylate, styrene, acrylonitrile and N-methylomethacrylamide, copolymers of N-methylolmethacrylamide and butanediol diacrylate, methyl acrylate and butyl acrylate, copolymers of ethyl acrylate, acrylonitrile and N-methylolacrylamide, copolymers of butyl acrylate and vinyl acetate with N-methylolacrylamide, copolymers of butyl acrylate, acrylonitrile and N-methylolacrylamide, copolymers of styrene, butyl acrylate and acrylic acid, natural latex or synthetic latexes of styrene with butadiene.

Preferred polymer dispersions are polyvinyl acetate dispersions (50% strength), copolymers of vinyl acetate with dibutyl maleate, for example in a ratio of 77/23 (about 50% strength), copolymers of styrene/butyl acrylate/acrylonitrile/methacrylic acid/acrylamide, for example in a ratio of 16:61:25:2:1 or 25:53:25:2:1, 6:3:1 copolymers of ethyl acrylate/acrylonitrile/N-methylolacrylamide, 35:55:10 copolymers of butyl acrylate/vinyl acetate/N-methylolacrylamide and also graft polymers (partially saponified), such as 50% polyvinyl alcohol, 25% polyvinyl acetate and 25% polyethylene or butadiene/styrene latex (about 50%), for example in a ratio of 40:60, 60:40 or 35:60+3.5 acrylic acid.

Plastic dispersions of this type are also used as a back finish for woven carpets, for the strengthening which produces the handle of the carpet.

In the case of tufted carpets, a back coating with natural latex or a synthetic latex dispersion, for example based on 40:60 or 60:40 butadiene/styrene is generally then also carried out.

The finishing liquors, both for the pre-coat and for the back coating of woven carpets, also contain thickeners.

As is known, the purpose of the thickener is to bring the finishes physically into a state which ensures that the impregnating liquor does not penetrate into the pile filament and stick these together during application.

Suitable thickeners are water-soluble hydroxyethylcelluloses, methylcelluloses, carboxymethylcelluloses, water-soluble starch products, partially etherified or etherified starch products, polyvinyl alcohols and the sodium or ammonium salts of alginic acid.

The pre-coat or also the carpet back coating for woven carpets can also be filled with chalk in the customary manner.

The process according to the invention for the flame-retardant finishing of woven fabrics, knitted fabrics, nonwoven fabrics and tufted or woven carpets is carried out under application conditions which are customary in the textile industry. An additional operation is not necessary.

The flame-retardant finishing liquors can be applied by a padding treatment, by means of a doctor blade or by nip-padding. The method used depends on the textile material. Woven fabrics or knitted fabrics are generally subjected to a padding treatment. Needle-punched nonwovens can be treated either on a padder or by means of doctor blade or nip-padding finishing.

The pre-coat impregnating liquor or the back finish for woven carpets is applied with the aid of an air knife, a rubber-bladed doctor or a cylindrical doctor.

Drying and/or curing is then carried out. The cotton fabric is first subjected to pre-drying at 80°–120° C. and is then cured for 4–5 minutes at 140°–160° C. Needle-punched nonwovens and tufted or woven carpets are dried at 130°–150° C.

Further finishing agents, such as textile softeners, products which impart hydrophobic properties, agents which impart oleophobic properties or antimicrobial finishing products, can also be added to the finishing liquors.

PREPARATION EXAMPLES (The following applies in general: because of side reactions, impurities and catalysts, the hydroxyl numbers found are always higher than those calculated. MR signifies the molar ratio between the compounds II and III. P-ODOP=2-propyl-2-oxo-1,3,2-di-oxa-phospholane)

EXAMPLE 1

(a) (MR=6.67, n=r=1, m=6.67)

26.8 g (0.1 mole) of oleyl alcohol are mixed, in the presence of a little thymolphthalein indicator, with 2.4 g (0.015 mole of NaOCH$_3$) of a 33% strength solution of sodium methylate in methanol. The methanol is stripped off in vacuo (1 mm Hg) at 30° C. and 100.0 g (0.667 mole) of 2-propyl-2-oxo-1,3,2-dioxa-pholane are added dropwise in the course of 50 minutes at about 5°–10° C., with continuous cooling. The reaction mixture remains deep blue during the dropwise addition and becomes decolorized only on prolonged standing at room temperature.

128 g of a slightly yellow colored oil with an acid number of 1 and a found hydroxyl number of 47 result. $P_{found}=15.9\%$ ($P_{calculated}=16.1\%$). It is water-soluble and foams slightly. A freshly prepared 1% strength aqueous solution has a turbidity point at 70° C.

(b) (MR=4.0, n=r=1, m=4.0)

The procedure is as in Example 1a. However, only 60.0 g (0.4 mole) of P-ODOP are added dropwise. 88 g of a yellowish oil with a hydroxyl number of 57 result. $P_{found}=13.8\%$ ($P_{calculated}=14.1\%$). A 1% strength aqueous solution has a turbidity point at 64° C.

(c) (MR=2.0; n=r=1, m=2)

26.8 g (0.1 mole) of oleyl alcohol are mixed only with 1.2 g (0.0075 mole of NaOCH$_3$) of a 33% strength solution of sodium methylate in methanol and only 30.0 g (0.2 mole) of P-ODOP are added dropwise. In other respects the procedure is as in Example 1a. 57 g of a yellowish oil which has a hydroxyl number of 91 result. $P_{found}$=10.7% ($P_{calculated}$=10.9%). The turbidity point of a 1% strength aqueous solution is at 55° C.

(d) (MR=1.0; n=r=1, m=1)

Only 0.6 g (0.0037 mole of NaOCH$_3$) of a 33% strength solution of sodium methylate in methanol is added to 26.8 g (0.1 mole) of oleyl alcohol. Only 15.0 g (0.1 mole) of P-ODOP are added dropwise. In other respects the procedure is analogous to Example 1a. 42 g of a yellowish oil with a hydroxyl number of 120 result. $P_{found}$=7.2% ($P_{calculated}$=7.3%). The substance is soluble only in a large amount of water (to give a turbid solution) and in 1% strength aqueous solution has an (indistinct) turbidity point at 45° C.

EXAMPLE 2

(a) (MR=10.0; n=r=1, m=10)

0.24 g (0.01 mole) of sodium hydride is dissolved at 50° C. in 36.4 g (0.1 mole) of tetrahydroperfluorooctanol + a trace of thymolphthalein. After the evolution of hydrogen has ceased—and after cooling to 25° C.-150.1 g (1 mole) of P-ODOP are added dropwise in the course of 30 minutes. The blue color of the indicator disappears on subsequent stirring.

187 g of a pale yellowish oil result; on dilution with water, this oil dissolves to give a clear solution and yields solutions which foam vigorously; the hydroxyl number is 37. $P_{found}$=16.3% ($P_{calculated}$=16.6%).

(b) (MR=4.0; n=r=1, m=4)

The procedure is analogous to Example 2a. However, only 60.0 g (0.4 mole) of P-ODOP are added dropwise.

96.5 g of a virtually colorless oil with a hydroxyl number of 64 result. $P_{found}$=12.6% ($P_{calculated}$=12.8%). The product gives only turbid solutions with water.

EXAMPLE 3

(MR=2.5; n=r=1, m=2.5)

0.5 g (0.003 mole of NaOCH$_3$) of a 33% strength solution of sodium methylate in methanol is added at 15° C. to a mixture of 6.4 g (0.2 mole) of methanol, a trace of thymolphthalein and 15 g (0.1 mole) of P-ODOP, with intensive cooling. After cooling the reaction, a further 60 g (0.4 mole) of P-ODOP are added dropwise in the course of 20 minutes to the deep-blue solution, which is still alkaline, with further cooling. On subsequent stirring at 25° C., the solution becomes colorless after 30 minutes.

82 g of an oil of low viscosity with a hydroxyl number of 25 result. $P_{found}$=18.5% ($P_{calculated}$=18.9%) $n_D^{20}$=1.4592

EXAMPLE 4

(MR=about 100; n=r=1, m=100)

0.5 g (0.003 mole of NaOCH$_3$ and 0.001 mole of methanol) of a 33% strength solution of sodium methylate in methanol is added all at once to 150.1 g (1 mole) of P-ODOP, which has been cooled to −8° C. Despite intensive cooling with CO$_2$/methanol, the temperature rises to 18° C.

150.5 g of a highly viscous oil with a P content of 20.3% ($P_{calculated}$=20.6%) and a found hydroxyl number of 14 result.

EXAMPLE 5

(MR=20; n=r=4, m=5)

6.8 g (0.05 mole) of pentaerythritol are dissolved in 150.1 g (1 mole) of P-ODOP at 80° C.—in the presence of a little thymolphthalein indicator. The solution is cooled to 15° C. 2 g (0.012 mole of NaOCH$_3$) of a 33% strength solution of sodium methylate in methanol are then added dropwise in the course of 15 minutes, at this temperature and with cooling, in such a way that the solution always remains blue in color, that is to say alkaline.

161 g of a viscous syrup with a hydroxyl number of 71 and a P content of 19.0% ($P_{calculated}$=19.2%) form.

EXAMPLE 6

(a) (MR=0.75; n=on average about 4, r=on average about 3, m=1)

8.0 g (about 0.05 mole of NaOCH$_3$) of a 33% strength solution of sodium methylate in methanol are added to 147.4 g (1 hydroxy equivalent) of an adduct of sucrose, glycerol and propylene oxide, which can be used to prepare a polyurethane rigid foam and has a hydroxyl number of 380, and a little thymolphthalein. The methanol is stripped off at 30° C. under an oilpump vacuum of 2 mm Hg. 112.6 g (0.75 mole) of P-ODOP are then added dropwise in the course of 60 minutes at 20°-25° C., with continuous cooling. The solution remains blue, that is to say alkaline, during this addition and is decolorized only on the addition of 0.5 ml of glacial acetic acid.

263 g of a colorless oil with a hydroxyl number of 261 and a P content of 8.7% ($P_{calculated}$=8.8%) result.

(b) (MR=0.5; n=about 4, r=about 2, m=1)

The procedure is as in Example 6a. However, only 1.6 g (0.01 mole of NaOCH$_3$) of a 33% strength solution of sodium methylate are used and only 75.0 g (0.5 mole) of P-ODOP are added dropwise. 223 g of a colorless oil with a hydroxyl number of 277 and a P content of 6.8% ($P_{calculated}$=6.9%) form.

(c) (MR=0.25; n=about 4, r=about 1, m=1)

Only 37.5 g (0.25 mole) of P-ODOP are added dropwise and in other respects the procedure is according to Example 6b. The virtually colorless oil (yield=186 g) has a hydroxyl number of 324 and a P content of 4.1% ($P_{calculated}$=4.2%).

(d) (MR=1.0; n=about 4, r=about 4, m=1)

3.3 g (0.02 mole of NaOCH$_3$) of a 33% strength solution of sodium methylate in methanol are used and 150.1 g (1 mole) of P-ODOP are added dropwise in the course of 90 minutes at 15°-20° C. In other respects the procedure is analogous to Example 6a.

299 g of a virtually colorless oil with a hydroxyl number of 220 and a phosphorus content of 10.2% ($P_{calculated}$=10.4%) result.

EXAMPLE 7

(a) (MR=12; n=r=3, m=4)

114.2 g (0.1 hydroxy equivalent) of an adduct of glycerol, propylene oxide and ethylene oxide, which has an average molecular weight of 3,500, a hydroxyl number of 47 and a proportion of primary hydroxyl groups of 20% and is used to prepare polyurethane flexible foams, and a spatula tip of thymolphthalein indicator are mixed at room temperature with 3.3 g (0.02 mole of NaOCH$_3$) of a 33% strength solution of sodium methylate in methanol. The methanol is stripped off under an oilpump vacuum of 1.5 mm Hg. 60.0 g (0.4 mole) of P-ODOP are then added dropwise at about 25° C., with mild continuous cooling. The viscosity of the reaction mixture, which is always alkaline (and blue in color) rises during this addition. At the end of the dropwise addition, the indicator is decolorized with 0.5 ml of glacial acetic acid and the pH is adjusted to 6.

Weight=176 g. The resulting viscous oil is colorless and has a hydroxyl number of 46 and a phosphorus content of 6.8% ($P_{calculated}=7.0\%$).

(b) (MR=9.0; n=r=3, m=3)

The procedure is as in Example 7a. However, only 1.6 g (0.01 mole of NaOCH$_3$) of a 33% strength solution of sodium methylate in methanol are used and only 45.0 g (0.3 mole) of P-ODOP are added dropwise.

160 g of a viscous, colorless oil with a hydroxyl number of 53 and a phosphorus content of 5.7% ($P_{calculated}=5.8\%$) form.

(c) (MR=6.0; n=r=3, m=2)

The procedure is analogous to Example 7b, but only 30.0 g (0.2 mole) of P-ODOP are added dropwise.

143 g of a colorless oil with a hydroxyl number of 47 and a phosphorus content of 4.2% ($P_{calculated}=4.3\%$) form.

EXAMPLE 8

(MR=4.0; n=r=2, m=2)

6.5 g (0.04 mole of NaOCH$_3$) of a 33% strength solution of sodium methylate in methanol are added to 21.0 g (0.2 mole) of diethanolamine and a little thymolphthalein at room temperature. The methanol is removed at 30° C. under a vacuum of 1.5 mm Hg. 120.1 g (0.8 mole) of P-ODOP are then added dropwise in the course of 50 minutes at 5°-12° C., with intensive continuous cooling. A distinctly discernible increase in the viscosity takes place during the addition.

Weight=143 g. The hydroxyl number found for the resulting deep blue (due to the indicator) oil is 209 and the phosphorus content is 17.0% ($P_{calculated}=17.3\%$). It can be confirmed by subsequent reactions, such as, for example, acylations, that the secondary amino group remains intact.

EXAMPLE 9

(MR=3.15; n=r=1, m=3.15)

4.9 g (0.03 mole of NaOCH$_3$) of a solution of sodium methylate in methanol are added to 52.5 g (0.5 mole) of 2-hydroxyethyl carbamate and a spatula tip of thymolphthalein. After stripping off the methanol under 2 mm Hg and at 30° C., 36.5 g (0.243 mole) of P-ODOP are first added dropwise in the course of 50 minutes at about 22° C. with continuous cooling. During this addition, the solution is decolorized and loses its alkalinity. After adding a further 4.9 g (0.03 mole of NaOCH$_3$) of the sodium methylate solution, a further 200 g (1.33 moles) of P-ODOP are added dropwise. The solution remains alkaline (or blue) until the addition is complete.

295 g of a colorless oil with a hydroxyl number of 144 and a phosphorus content of 16.2% ($P_{calculated}$ 15.6%) result.

EXAMPLE 10

(MR=3.5; n=r=1, m=3.5)

3.3 g (0.02 mole of NaOCH$_3$) of a 33% strength solution of sodium methylate in methanol are added to 26 g (0.2 mole) of 2-hydroxyethyl methacrylate, 0.1 g of hydroquinone monomethyl ether and a spatula tip of thymolphthalein, at 5°-10° C., and the methanol is stripped off under 1.5 mm Hg. 105.1 g (0.7 mole) of P-ODOP are then added dropwise in the course of 2 hours at 5°-10° C.

Weight=134.5 g. The viscous reaction mixture has a hydroxyl number of 99 and a phosphorus content of 15.8% ($P_{calculated}=16.1\%$). It polymerizes on heating with agents which form free radicals, such as, for example, azo-diisobutyronitrile.

EXAMPLE 11

(MR=5.0; n=r=1, m=5)

First a little thymolphthalein indicator and then 0.6 g (about 0.025 mole) of sodium hydride are stirred into 27.0 g (0.1 mole) of molten octadecyl alcohol at 60° C., until the mixture is homogeneous. A total of 75 g (0.5 mole) of P-ODOP are then added dropwise to the deep blue melt in the course of 25 minutes, first at 60° C. and—when about one fifth of the total amount has been added—then at 40°-45° C. The melt remains deep blue during the addition.

After adding 0.5 ml of glacial acetic acid, 102 g of a slightly yellow colored waxy mass with a hydroxyl number of 68 and a phosphorus content of 15.0% ($P_{calculated}=15.2\%$) result. The reaction product is soluble in water and gives foaming solutions.

EXAMPLE 12

(MR=3.0; n=r=1, m=3)

4.9 g (0.03 mole of NaOCH$_3$) of a 33% strength solution of sodium methylate in methanol are added to 29.0 g (0.5 mole) of allyl alcohol. After stripping off the methanol at 25° C. and under 12 mm Hg, 3 g of the allyl alcohol which has also been distilled off are added again and, at 10° C., 225.1 g (1.5 moles) of P-ODOP are added dropwise in the course of 50 minutes, with continuous cooling.

255 g of a colorless oil with a hydroxyl number of 142, a phosphorus content of 18.0% ($P_{calculated}=18.2\%$) and a refractive index $n_D^{20}=1.4670$ result.

EXAMPLE 13

(MR=1.0; n=2, r=1, m=1)

62.1 g (1 mole) of glycol, a little thymolphthalein and 1.6 g (0.01 mole of NaOCH$_3$) of a 33% strength solution of sodium methylate in methanol are mixed at room temperature and the methanol is stripped off under a pump vacuum at 20° C. 150.1 g (1 mole) of P-ODOP are added dropwise at 5°-8° C. in the course of 60 minutes, with continuous cooling. The reaction mixture remains alkaline (or blue due to the indicator) during the addition. Only on subsequent stirring does it decolorize itself due to side reactions.

213.5 g of a colorless oil with a hydroxyl number of 550, a phosphorus content of 14.2% ($P_{calculated}=14.5\%$) and a refractive index $n_D^{20}=1.4602$ result.

EXAMPLE 14

(MR=1.3; n=r=1, m=1.3)

1.6 g (0.01 mole of NaOCH$_3$) of a 33% strength solution of sodium methylate in methanol are added to 30.4 g (0.2 mole) of 2-hydroxyethyl methyl-ethyl-phosphinate at 0°-10° C. The methanol is stripped off at 10° C. and 1.5 mm Hg. 39 g (0.26 mole) of P-ODOP are then added dropwise in the course of 5 minutes with intensive cooling.

Weight=70 g. The resulting oil is slightly yellow in color and has a hydroxyl number of 170 and a refractive index of $n_D^{20}=1.4672$. $P_{found}=19.9\%$ ($P_{calculated}=20.3\%$)

EXAMPLE 15

(MR=2.0; n=r=1, m=2)

A total of 1.5 g (0.0092 mole) of a 33% strength solution of sodium methylate in methanol are added dropwise in the course of 15 minutes to a mixture of 9 g (0.1 mole) of methyl glycolate, a little thymolphthalein and 30 g (0.2 mole) of P-ODOP, at 5°–10° C. and with intensive cooling, at such a rate that the reaction mixture always remains just still blue-colored, that is to say alkaline.

39.5 g of a yellowish oil with a hydroxyl number of 177, a phosphorus content of 15.5% ($P_{calculated}$=15.7%) and a refractive index $n_D^{20}$=1.4570 result.

EXAMPLE 16

(MR=about 48; n=r=1, m=about 48)

0.3 g (0.0018 mole of $NaOCH_3$ and 0.0063 mole of $CH_3OH$) of a 33% strength solution of sodium methylate in methanol is added in the course of 10 minutes to 57.6 g (0.3 mole) of 2-n-hexyl-2-oxo-1,3,2-di-oxa-phospholane and a spatula tip of thymolphthalein, at 10°–20° C. with intensive cooling, at such a rate that the solution always remains slightly blue, that is to say alkaline. On subsequent stirring at room temperature, the alkalinity disappears as a result of side reactions.

Weight=57.7 g. The reaction product is obtained in the form of a viscous colorless oil with a hydroxyl number of 23, a phosphorus content of 15.8% ($P_{calculated}$=16.1%) and a refractive index $n_D^{20}$=1.4706. It is only partially soluble in water and in water has a pH value of 6.

EXAMPLE 17

(MR (in total)=32.0; n=r=1, m=32)

0.3 g (0.00185 mole of $NaOCH_3$ and 0.00625 mole of methanol) of a 33% strength solution of sodium methylate in methanol is added dropwise in the course of 30 minutes to 22.0 g (0.1 mole) of 2-n-octyl-2-oxo-1,3,2-dioxa-phospholane, 13.1 g (0.1 mole) of 2-ethyl-2-oxo-1,3,2-dioxa-phospholane and a spatula tip of thymolphthalein, at 5°–15° C. and with intensive cooling, at such a rate that the reaction mixture always remains just slightly blue, that is to say alkaline. 35 g of a viscous colorless oil with a phosphorus content of 17.3% ($P_{calculated}$=17.7%) and a refractive index $n_D^{20}$=1.4696 result. The oil dissolves in water to give a clear solution. The aqueous solution foams vigorously and becomes turbid on warming.

EXAMPLE 18

(MR=4.5; n=r=3, m=1.5)

6.1 g (0.067 mole) of glycerol, a little thymolphthalein and 49.2 g (0.3 mole) of 2-n-butyl-2-oxo-1,3,2-dioxaphospholane are cooled to 5° C. and, at 5° C., 1 g (0.0062 mole of $NaOCH_3$) of a 33% strength solution of sodium methylate in methanol is added in the course of 30 seconds, with intensive cooling. Despite the cooling, the temperature rises to 20° C. during this addition. However, the reaction mixture still remains blue, that is to say alkaline.

Weight=56 g. The reaction product is obtained in the form of a viscous colorless oil with a hydroxyl number of 226, a phosphorus content of 16.5% ($P_{calculated}$=16.8%) and a refractive index $n_D^{20}$=1.4691.

EXAMPLE 19

(MR=2.0; n=r=1, m=2)

2 g (0.0125 mole of $NaOCH_3$) of a 33% strength solution of sodium methylate in methanol are added in the course of 10 minutes to 18.8 g (0.2 mole) of 1-chloropropan-2-ol, a little thymolphthalein and 60.0 g (0.4 mole) of P-ODOP, at 5° C., with cooling.

Weight=about 81 g. The colorless oil, which is of low viscosity, has a refractive index $n_D^{20}$=1.4601, a hydroxyl number of 263 and a phosphorus content of 15.1% ($P_{calculated}$=15.3%).

EXAMPLE 20

(MR=3.0; n=r=2, m=3)

23.2 g (=0.2 mole) of 1,4-cyclohexanediol and a little thymolphthalein are dissolved in 30 g of tetrahydrofuran at 60° C. After cooling to 10° C., 2 g of a 33% strength solution of sodium methylate in methanol are added dropwise and then 90 g (0.6 mole) of P-ODOP are added dropwise in the course of 15 minutes at 10°–15° C., with intensive cooling. In order to maintain the alkaline medium, a further 2 g of the sodium methylate solution are added during this addition. The tetrahydrofuran is stripped off under a waterpump vacuum.

117 g of a colorless oil remain. ($n_D^{20}$=1.4802, OH number=301, $P_{found}$=15.8% ($P_{calculated}$=15.9%).

EXAMPLE 21

(MR=6.0; n=r=3, m=2)

2 g of a 33% strength solution of sodium methylate in methanol are added in the course of 60 minutes to a mixture of 7.1 g (0.083 mole) of glycerol and 75 g (0.5 mole) of P-ODOP, at 25° C., with cooling.

86 g of a colorless viscous oil which has a refractive index $n_D^{20}$=1.4686 result. $P_{found}$=18.0% ($P_{calculated}$=18.3%).

EXAMPLE 22

(MR=20, n=r=3, m=6.67)

2.5 g of a 33% strength solution of sodium methylate in methanol are added in the course of 10 minutes to a mixture of 3.0 g (0.02 mole) of triethanolamine and 60 g (0.4 mole) of P-ODOP, at 20° C., with cooling.

65.5 g of a colorless viscous oil with a refractive index $n_D^{20}$=1.4677 result. $P_{found}$=18.6% ($P_{calculated}$=18.9%).

EXAMPLE 23

(MR=20; n=r=2, m=10)

2.8 g of a 33% strength solution of sodium methylate in methanol are added in the course of 20 minutes to 60 g (0.01 mole) of polyethylene glycol 6,000, 60 g of tetrahydrofuran and 30 g (0.2 mole) of P-ODOP, at 20°–25° C., with cooling. The tetrahydrofuran is stripped off under a waterpump vacuum. The residue (=91.5 g) has a solidification point of 48° C.

The hydroxyl number found is 36 and the phosphorus content is 6.6% ($P_{calculated}$=6.8%).

EXAMPLE 24

(MR=5.0; n=r=2, m=5)

A little thymolphthalein and 3 g of a 33% strength solution of sodium methylate in methanol are added to 24.4 g (0.2 mole) of bis-(2-hydroxyethyl) sulfide. The methanol is stripped off under 2 mm Hg. Then, first 25 g of P-ODOP are added dropwise in the course of 15 minutes, with cooling, and, after adding a further 3 g of the sodium methylate solution, a further 125 g of P-ODOP (that is to say the total amount is 1 mole) are added dropwise in the course of 20 minutes.

177 g of an oil with a refractive index $n_D^{20} = 1.4767$, a hydroxyl number of 224 and a phosphorus content of 17.3% ($P_{calculated} = 17.5\%$) result.

EXAMPLE 25

(MR=2; n=r=1, m=2)

52 g (0.5 mole) of N-2-hydroxyethyl-urea and a little thymolphthalein are dissolved in 150 g (1.0 mole) of P-ODOP and 2.5 g of a 33% strength solution of sodium methylate in methanol are added dropwise at 7° C. in the course of 10 minutes, with cooling.

The resulting 154 g of a viscous colorless oil have a refractive index of $n_D^{20} = 1.4740$, a hydroxyl number of 131 and a phosphorus content of 17.4% ($P_{calculated} = 17.8$).

EXAMPLE 26

(MR=3.0; n=r=1, m=3)

5 g of a 33% strength solution of sodium methylate in methanol are added dropwise in the course of 20 minutes to 30.8 g (0.2 mole) of dimethyl 2-hydroxyethane-phosphonate, a little thymolphthalein and 73.2 g (0.6 mole) of 2-methyl-2-oxo-1,3,2-dioxa-phospholane, at 5° C., with intensive cooling. The reaction mixture is still alkaline (or blue-colored) even at the end of the addition. It decolorizes only after standing for 3 hours at room temperature.

109 g of a colorless oil with a refractive index $n_D^{20} = 1.4605$, a hydroxyl number of 338 and a phosphorus content of 22.3% ($P_{calculated} = 22.7\%$) result.

EXAMPLE 27

(MR=10; n=r=1, m=10)

16 g (0.05 mole) of 2-hydroxyethyl methyl-tetradecylphosphinate are dissolved in 75 g (0.5 mole) of P-ODOP and 2.5 g of a 33% strength solution of sodium methylate in methanol are added dropwise in the course of 15 minutes at 6° C., with cooling.

93 g of a colorless oil with a refractive index $n_D^{20} = 1.4665$, a hydroxyl number of 79 and a phosphorus content of 18.2% ($P_{calculated} = 18.3\%$) result.

EXAMPLE 28

(MR=15; n=r=3, m=5)

1 g of a 33% strength solution of sodium methylate in methanol is added in the course of 20 minutes to a mixture of 3.07 g (0.033 mole) of glycerol, a little thymolphthalein and 67 g (0.5 mole) of 2-vinyl-2-oxo-1,3,2-dioxa-phospholane, at 2° C., with intensive cooling.

71 g of a colorless oil with a refractive index $n_D^{20} = 1.4718$, a hydroxyl number of 133 and a phosphorus content of 21.1% ($P_{calculated} = 21.8\%$) result.

The product crosslinks on warming with free radical polymerization catalysts.

EXAMPLE 29

(MR=about 9.5; n=r=1, m=about 9.5)

1 g (=0.021 mole of $CH_3OH$ and 0.0062 mole of $NaOCH_3$) of a 33% strength solution of sodium methylate in methanol is added dropwise in the course of 15 minutes to 51.2 g (0.2 mole) of a mixture of stereoisomers of the formula

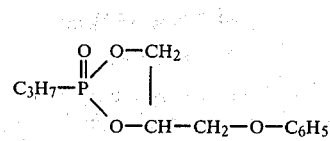

at 40° C., with intensive cooling. The reaction product (=52 g) is highly viscous and has a refractive index of $n_D^{20} = 1.5152$, a hydroxyl number of 34 and a P content of 11.8% ($P_{calculated} = 11.9\%$).

EXAMPLE 30

(MR (in total)=12; n=r=1, m=12)

1.2 g (=0.025 mole of methanol and 0.007 mole of $NaOCH_3$) of a 33% strength solution of sodium methylate in methanol are added in the course of 20 minutes to 39.7 g (0.2 mole) of a mixture of stereoisomers of the formula

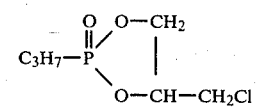

and 15.6 g (0.1 mole) of 2-chloromethyl-2-oxo-1,3,2-dioxa-phospholane, at 6° C., with intensive cooling.

Yield: 56.5 g.

The viscous oil has a refractive index of $n_D^{20} = 1.4862$, a hydroxyl number of 35 and a phosphorus content of 16.1% ($P_{calculated} = 16.4\%$).

EXAMPLE 31

(MR=5.0; n=r=1, m=5)

10.8 g (0.1 mole) of benzyl alcohol, 75 g (0.5 mole) of P-ODOP and 0.5 of sodium carbonate are heated to 150° C., and kept at 150° C. for 30 minutes, whilst passing nitrogen over the mixture.

The reaction mixture (=86 g) dissolves in water to give a clear solution, which is not the case with the unreacted mixture of the starting materials.

$n_D^{20} = 1.4750$. The hydroxyl number is 145.

P content = 17.7% ($P_{calculated} = 18.0\%$).

With twice the amount of benzyl alcohol (MR=2.5 and m=2.5), a water-soluble colorless oil (with a refractive index $n_D^{20} = 1.4847$, a hydroxyl number of 168 and a P content of 15.7% ($P_{calculated} = 16.0\%$)) is likewise obtained.

EXAMPLE 32

(a) (MR=8; n=r=1, m=8)

18.2 g (0.05 mole) of tetrahydro-perfluoro-octanol, 60.0 g (0.4 mole) of P-ODOP and 0.5 g of sodium carbonate are heated to 150° C. and kept at 150° C. for 80 minutes. After cooling, a colorless oil results and this can be diluted with water to give a clear solution and gives solutions which foam vigorously. $n_D^{20} = 1.4461$. $P_{found} = 15.4\%$ ($P_{calculated} = 15.7\%$) acid number = 10.6, hydroxy number = 85.

(b) (MR=8; n=r=1, m=8)

The procedure is as in Example 32a but without the addition of sodium carbonate. However, after stirring for 80 minutes at 150° C., the reaction mixture is still not soluble in water to give a clear solution (with foaming); this is the case only after 6 hours.

$n_D^{20} = 1.4400$. The acid number is 13.2 and the hydroxyl number 105. $P_{found} = 15.4\%$ ($P_{calculated} = 15.7\%$).

USE EXAMPLES

EXAMPLE 1

A tufted broadloom carpeting with a weight per square meter of 650 g and with a polyamide loop pile, 6 mm high, tufted onto a support material of needle-punched polypropylene nonwoven fabric is used for the tests.

The pre-coat impregnating solution has the following composition: 300 parts of a reaction product, prepared according to Example 21, of 1 mole of glycerol and 6 moles of

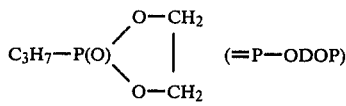

130 parts of an 80% strength trimethylol-melamine trimethyl ether solution, 150 parts of a 50% strength butadiene/styrene dispersion (60:40), 300 parts of a 3.5% strength methyl-hydroxyethylcellulose solution, 5 parts of ammonium chloride, 400 parts of chalk and 200 parts of water.

The pre-coat is applied with the aid of a hand doctor and dried for 16 minutes at 140° C. The amount of dry coating is about 835 g/m².

The pile filaments are very firmly fastened in the base fabric and display their original mobility, since the impregnating solution for the pre-coat has not penetrated into the pile. The tufted carpet has a flexible handle.

In comparison to the above, a cut piece of the tufted goods described above is provided with a pre-coat which does not contain any flame-retardant components. Binding of the pile filaments is again effected with a 50% strength butadiene/styrene dispersion (60:40), to which chalk and methyl-hydroxyethylcellulose solution, as thickener, are added.

Both cut pieces of carpet are tested according to DIN 54,332, the time of exposure to the flame being 15, 30 and 60 seconds. The cut piece of carpet which has not been provided with a flame-retardant finish burns away after the test flame is removed. The cut piece of carpet provided with a flame-retardant finish displays no further burning or smouldering after the test flame is removed.

The very good flame-retardant effect is also still discernible after shampooing four times or after several wet treatments.

EXAMPLE 2

A cut piece of tufted carpet which has a weight per square meter of 700 g and consists of a needle-punched polypropylene nonwoven fabric and a green colored polyester pile, with a pile height of about 5.5 mm, is treated with a precoat composition which is made up as follows: 280 parts of a reaction product, prepared according to Example 22, of 1 mole of triethanolamine+20 moles of

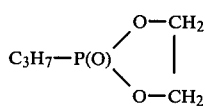

(=P-ODOP), 140 parts of an 80% strength trimethylol-melamine trimethyl ether solution, 180 parts of a 50% strength butadiene/styrene dispersion (60:40), 350 parts of a 3.5% strength methyl-hydroxyethylcellulose solution, 5 parts of ammonium chloride, 400 parts of chalk and 200 parts of water.

The pre-coat is carried out as in Example 1. After curing (15 minutes at 145° C.), the amount of dry coating is about 810 g/m². The tufted carpet provided with the flame-retardant finish meets the requirements of DIN test method 54,332 with times of exposure to the flame of 15, 30 and 60 seconds. The cut piece of carpet does not continue to burn after the flame is removed. After finishing, the pile displays its original mobility; the impregnating composition for the pre-coat has not penetrated into the pile.

EXAMPLE 3

The tufted carpet described in Example 1 is treated with a pre-coat impregnating solution of the following composition: 320 parts of a reaction product, prepared analogously to Example 9, of 1 mole of HO—C$_2$H$_4$—O—CO—NH$_2$+2 moles of

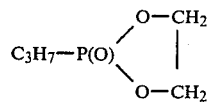

(=P-ODOP), 170 parts of an 80% strength trimethylol-melamine trimethyl ether solution, 170 parts of a 50% strength butadiene/styrene dispersion (60:40), 350 parts of a 3.5% strength methyl-hydroxyethylcellulose solution, 4 parts of ammonium chloride, 380 parts of chalk and 210 parts of water.

Finishing is carried out as described in Example 1. This tufted material also withstands the flame-retardant test according to DIN 54,332, with times of exposure to the flame of 15, 30 and 60 seconds. The flame-retardant effect is fully retained even after shampooing three times.

The tufted goods provided with a flame-retardant finish have a flexible handle.

EXAMPLE 4

The tufted goods described in Example 1 are provided with a pre-coat impregnating solution of the following composition: 300 parts of a reaction product, prepared according to Example 10, of 1 mole of 2-hydroxyethyl methacrylate+3.5 moles of P-ODOP, 80 parts of a 50% strength N,N'-dimethylol-methylene-bis-acrylamide solution, 50 parts of an 80% strength trimethylol-melamine trimethyl ether solution, 20 parts of carbamide-hydrogen peroxide, 1 part of potassium persulfate, 200 parts of a 50% strength butadiene/styrene dispersion (60:40), 350 parts of a 3.5% strength methyl-hydroxyethylcellulose solution and 400 parts of chalk.

The pre-coat is applied with the aid of a hand doctor and dried for 14 minutes at 135°–140° C. The amount of dry coating is about 850 g/m².

The flame-retardant finish is excellent. The cut pieces of carpet meet the requirements of DIN 54,322 "Determination of the Combustion Characteristics of Textile Floor Coverings" and DIN 54,333, "Determination of the Speed of Flame Propagation on Textiles".

After removing the test flame—after 15 seconds, 30 seconds and 60 seconds for DIN 54,332 and after 15 seconds for DIN 54,333—the carpet does not continue to burn and does not smoulder. The flame-retardant effect survives several shampoo treatments.

EXAMPLE 5

A needle-punched nonwoven broadloom carpeting, consisting of a fiber mixture of 50% of polyamide 6 and 50% of polyester fibers, with a weight per square meter of 750 g, which is used as broadloom carpeting in living rooms, is treated on a two-roll padder with an aqueous impregnating solution of the following composition: 300 g/l of a reaction product, prepared according to Example 10, of 1 mole of hydroxyethyl methacrylate+3.5 moles of P-ODOP, 85 g/l of a 50% strength N,N'-dimethylolmethylene-bis-acrylamide solution, 60 g/l of an 80% strength trimethylol-melamine trimethyl ether solution, 20 g/l of carbamide-hydrogen peroxide, 2 g/l of potassium persulfate and 350 g/l of a 40% strength aqueous plastic dispersion of a copolymer of ethyl acrylate/acrylonitrile/N-methylolacrylamide in a ratio of 6:3:1.

The pick-up is about 105%. Drying is carried out for 20 minutes at 145° C.

The needle-punched felt is elastic and has good dimensional stability. The permanent flameproofing survives several low-temperature washes at 50° C. and several shampoo treatments.

The flameproofing test is carried out according to DIN 54,333. A test piece of the same needle-punched nonwoven is finished with 350 g/l of the abovementioned 40% strength plastic dispersion. It continues to burn after the test flame is removed and the burn covers an interval length of 10 cm at a burning rate of 2 minutes and 30 seconds.

The test piece provided with a flame-retardant finish, on the other hand, smoulders for 5 seconds after the flame is removed, but the burn does not spread.

After shampooing four times, a smouldering time of 30 seconds is found. After this time the flame has gone out. However, the flame has not spread further.

EXAMPLE 6

A needle-punched felt broadloom carpeting of the type described in Example 5 is treated on a padder with the following impregnating solution. The pick-up is about 100%. Drying is carried out at 150° C. for 18 minutes.

280 g/l of a reaction product, prepared analogously to Example 3, of 1 mole of $CH_3OH$ and 5 moles of P-ODOP, 150 g/l of an 80% strength trimethylolmelamine trimethyl ether solution, 300 g/l of a 40% strength plastic dispersion of a copolymer of ethyl acrylate/acrylonitrile/N-methylolacrylamide in a ratio of 6:3:1 and 5 g/l of ammonium chloride.

The flexible and dimensionally stable needle-punched felt displays a very good permanent flame-retardant effect according to DIN 54,333. The needle-punched felt smoulders for 15 seconds after removal of the test flame. After shampooing three times, the felt smoulders for 45 seconds.

We claim:

1. Organic phosphorus compounds with 2-hydroxyalkylphosphonic acid groups of the general formula I

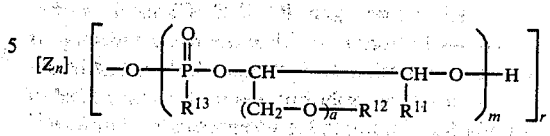

the individual symbols in the above formula I having the following meaning: n is an integer of 1 to 6, r is an integer from 1 to 6; m is 1 if $r > n$ or is a number from 1 to 150; a is 0 or 1; $R^{11}$ is a saturated or unsaturated or branched alkyl radical with 1–5 carbon atoms or, hydrogen, $R^{12}$ is saturated or unsaturated or branched alkyl radical with 1–22 carbon atoms, which may be substituted by 1 or two chlorine or bromine atoms, or a cycloalkyl radical with 6–10 carbon atoms, an aryl or aralkyl radical with up to 18 C atoms, or crotonyl, acroyl or methacroyl or—but only if a=0—hydrogen, and $R^{13}$ has the same meaning as $R^{12}$ with the exception of hydrogen and can additionally be a monovalent phosphorus-containing radical of the formula $R_p^{13}$

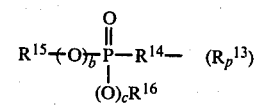

in which b and c represent 0 or 1, $R^{14}$ represents $C_1$-$C_{10}$-alkylene, cycloalkylene, arylene or aralkylene, and also $R^{15}$ and $R^{16}$ represent saturated or unsaturated or branched $C_1$-$C_5$-alkyl radicals; and $z_n$ is a n-valent radical from the group comprising straight-chain or branched aliphatic or araliphatic hydrocarbon radicals with 1 to 22 which may be interrupted by up to two carboxylate groups (—C—CO—) or up to 2 —S— or $NR^2$ radicals in which $R^2=(C_1$—$C_4)$-alkyl, or substituted by fluorine, chlorine or bromine atoms or carboalkoxy groups or carboxamide, carbamate or urea groups or by primary, secondary or tertiary amino groups, or hydrocarbon radicals which contain ether groups and have equivalent weights of up to 8000 and are obtained by oxethylation or oxpropylation of n-valent aliphatic, araliphatic or aromatic hydroxy compounds, amines or mono-or di-carboxylic acids with 1–22 C atoms, in which the araliphatic or the aromatic radicals are derived from benzene, alkyl- or alkylene=-benzenes with up to 18 C atoms, naphthalene, diphenyl, diphenylmethane, diphenylethane or 2,2-diphenylpropane and may be substituted in the nucleus by 1 ro 2 methoxy or ethoxy groups or can be substituted, in the nucleus or on the side chains by F, Cl or Br atoms, or phosphorus-containing radicals of the general formula

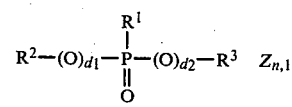

in which $d_1$ and $d_2$ independently of one another are 0 and 1 and $R^1$ is alkyl, hydroxyalkyl, ($C_1$-$C_2$)-alkylated or -dialkylated aminoalkyl, halogeno- alkyl with 1 to 3 C atoms, alkenyl with 2 or 3 C atoms or phenyl, which may be substituted by 1 or 2 halogen atoms, and $R^2$ and $R^3$ have the same meaning as $R^1$ with the proviso that at least one of the radicals $R^2$ or $R^3$ is an alkylene radical with 2–5 C atoms.

2. Compounds as claimed in claim 1 wherein n and r are identical and are an integer from 1 to 4, m is 2 to 10, a is 0 or 1, $R^{11}$ is hydrogen, $R^{12}$ is $C_1$-$C_3$-alkyl or—but only if a=0—hydrogen, $R^{13}$ has the same meaning as $R^{12}$ with the exception of hydrogen and can additionally be a monovalent phosphorus—containing radical of the formula $R_p{}^{13}$ in which b and c represent 0 or 1, $R^{14}$ is $C_1$-$C_1$-alkylene and $R^{15}$ and $R^{16}$ are methyl or ethyl and $Z_n$ is as defined in claim 1.

3. Process for the manufacture of the phosphorus compounds as claimed in claim 1, which comprises reacting, in the presence of a strongly alkaline catalyst at a temperature of from 0°–40°, 1 mole of a compound of the general formula II $$Z_n(OH)_n \quad (II)$$

with 1 to n.0.25 moles of 2-oxo-1,3,2-dioxa-phospholanes of the general formula III

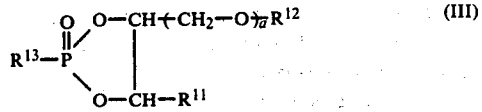

which are substituted in the 2-position and in which formulae n, a, $R^{11}$, $R^{12}$, $R^{13}$ and Z are defined in claim 4.

* * * * *